United States Patent [19]

Slovacek et al.

[11] Patent Number: 5,340,715
[45] Date of Patent: Aug. 23, 1994

[54] MULTIPLE SURFACE EVANESCENT WAVE SENSOR WITH A REFERENCE

[75] Inventors: Rudolf E. Slovacek, Norfolk, Mass.; Walter F. Love, Horseheads; Thomas A. Cook, Corning, both of N.Y.; Richard L. Schulkind, Sharon; Irene M. Walczak, Boston, both of Mass.

[73] Assignee: Ciba Corning Diagnostics Corp., Medfield, Mass.

[21] Appl. No.: 711,783

[22] Filed: Jun. 7, 1991

[51] Int. Cl.⁵ ............................................. G01N 33/552
[52] U.S. Cl. ............................................ 435/6; 422/57; 422/82.05; 422/82.07; 422/82.08; 422/82.11; 435/174; 435/176; 435/182; 435/291; 435/808; 436/164; 436/172; 436/518; 436/527; 436/805; 436/807; 385/12; 385/141; 385/142; 385/143
[58] Field of Search ............... 385/12, 141, 142, 143; 422/57, 82.05, 82.06, 82.07, 82.08, 82.09, 82.11; 435/6, 174, 176, 177, 180, 181, 182, 291, 808; 436/518, 527, 164, 172, 805, 807

[56] References Cited

U.S. PATENT DOCUMENTS

| | | | |
|---|---|---|---|
| 4,050,895 | 9/1977 | Hardy et al. | 436/805 |
| 4,558,014 | 12/1985 | Hirschfeld et al. | 436/808 |
| 4,775,637 | 10/1988 | Sutherland et al. | 422/82.11 |
| 4,842,783 | 6/1989 | Blaylock | 385/12 |
| 4,846,548 | 7/1989 | Klainer | 385/12 |
| 4,880,752 | 11/1989 | Keck et al. | 436/807 |
| 5,001,051 | 3/1991 | Miller et al. | 435/6 |
| 5,156,976 | 10/1992 | Slovacek et al. | 422/82.11 |

OTHER PUBLICATIONS

Halliday et al, *Physics*, (John Wiley & Sons, New York), 1978, p. 947.

*Primary Examiner*—Toni R. Scheiner
*Assistant Examiner*—Christopher L. Chin
*Attorney, Agent, or Firm*—Nicholas I. Slepchuk, Jr.; Arthur S. Morgenstern; Judith A. Roesler

[57] ABSTRACT

An evanescent wave sensor and method for use in analyzing one or more media, the sensor including a waveguide having first and second wave propagating surfaces. The waveguide propagates an input signal along the waveguide between the first and second surfaces. The first surface receives a first radiation signal which indicates the presence of a first analyte, and the second surface receives a second radiation signal representing one or both of a second analyte and a reference. The first and second surfaces can both be contacted with a single medium, or with two separate media, and one or more output signals can be detected.

26 Claims, 10 Drawing Sheets

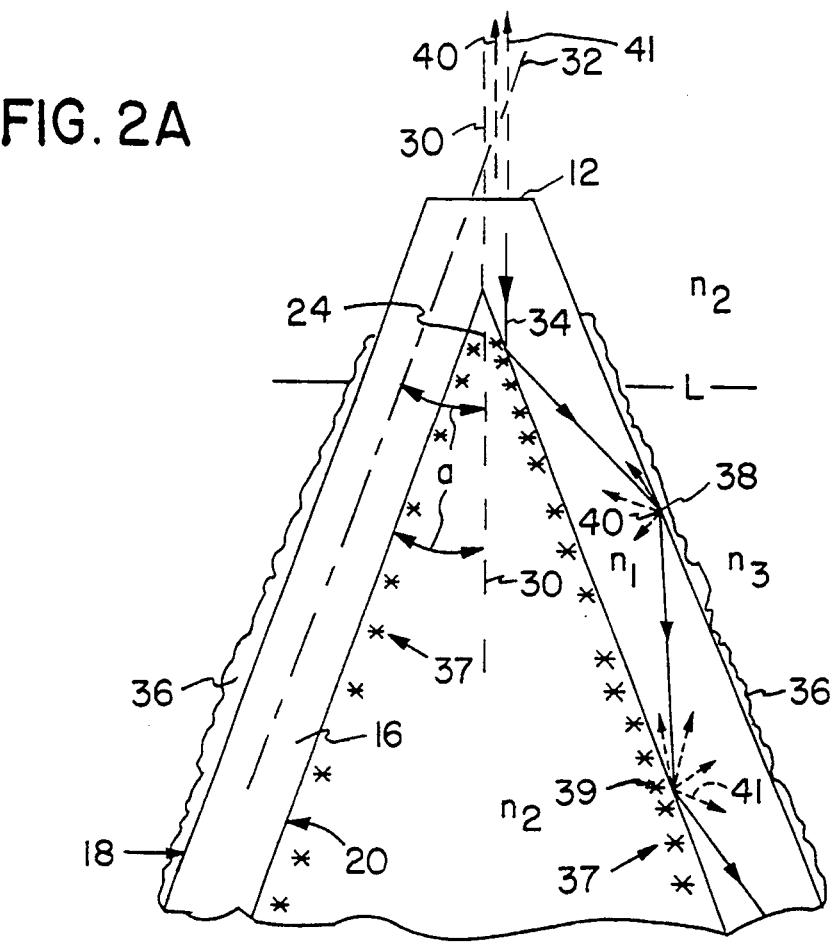
FIG. 2A
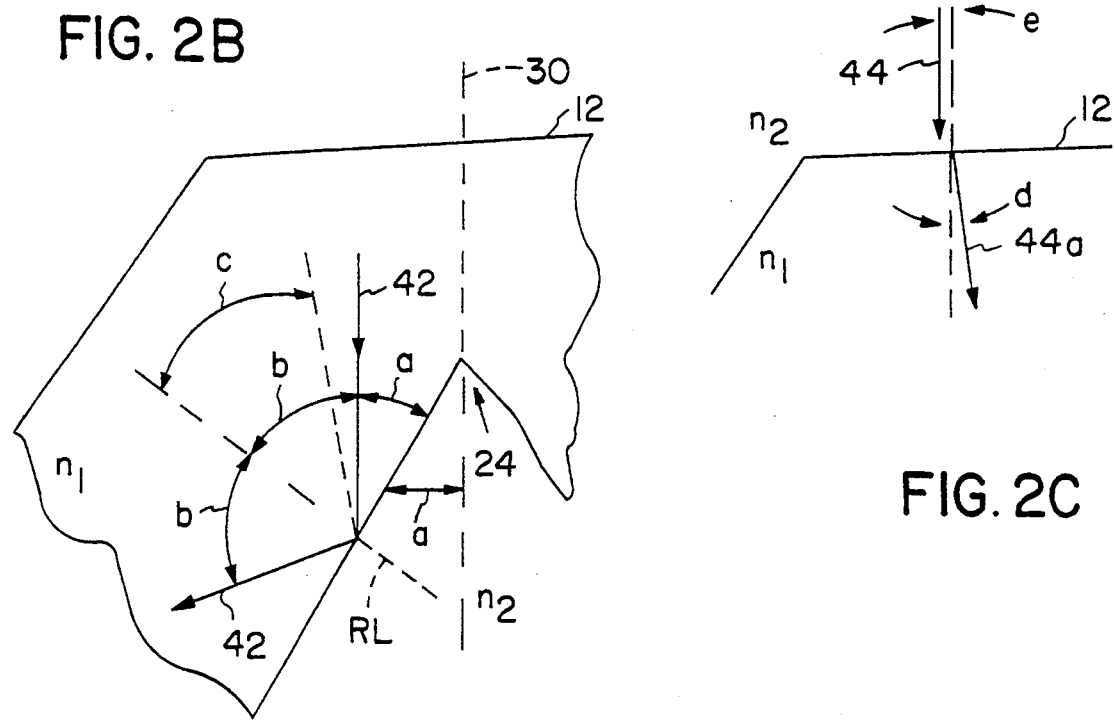
FIG. 2B
FIG. 2C

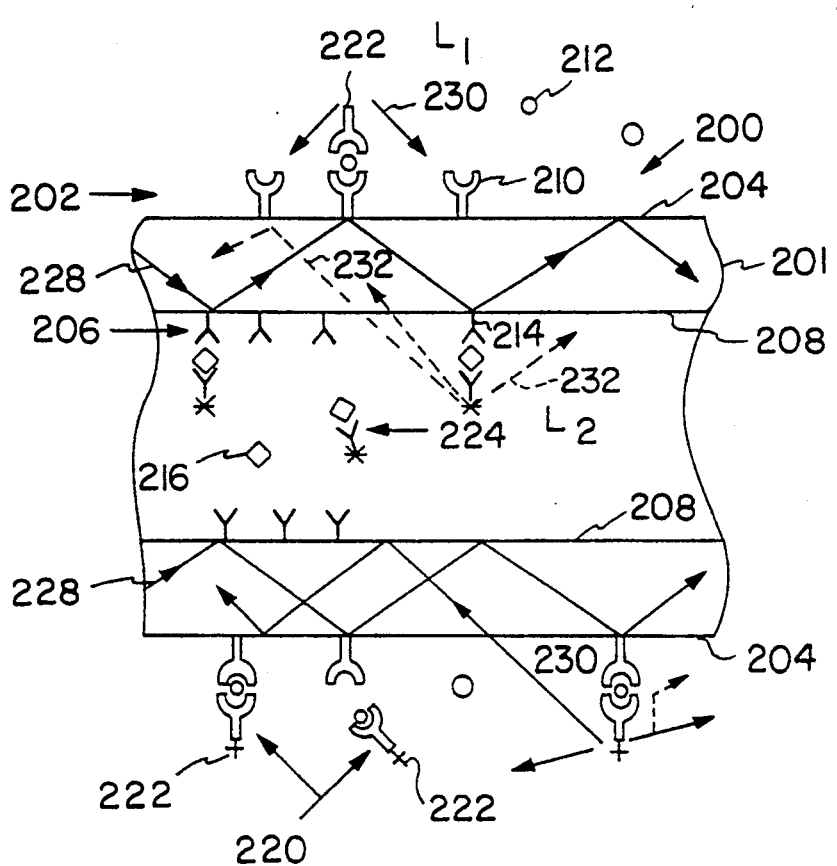
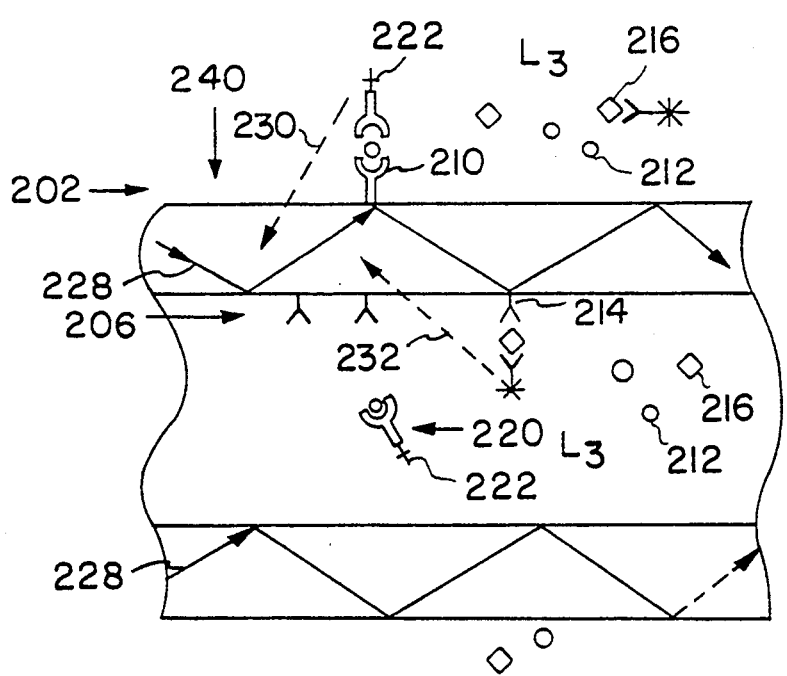
FIG. 3
FIG. 4

MULTIPLE SURFACE EVANESCENT WAVE SENSOR WITH A REFERENCE

FIELD OF THE INVENTION

This invention relates to improved evanescent wave sensors for use in spectrophotometric signal responsive processing assays of analytes in fluids, and more particularly to such sensors having at least two optical surfaces which carry one or more fluoromeres and/or a reactive coating.

CROSS-REFERENCES

The following applications, filed concurrently with, are incorporated herein by reference: Slovacek et al., U.S. patent application Ser. No. 07/712,003, now U.S. Pat. No. 5,156,976, entitled "Evanescent Wave Sensor Shell and Apparatus"; and Slovacek et al., U.S. patent application Ser. No. 07/712,304 entitled "Multiple Output Referencing System For An Evanescent Wave Sensor".

TECHNICAL DISCLOSURE

There are a number of optical devices which propagate radiation by total internal reflection to generate an evanescent wave at the interface of the device and a surrounding medium having a lower index of refraction. See Harrick, N.J., Internal Reflection Spectroscopy, Hatrick Scientific Corp., Ossinging, N.Y. (Third Printing 1987). The evanescent wave is an electromagnetic waveform which typically extends less than a wavelength into the surrounding medium. However, this penetration is sufficient to permit substantial optical interaction between the evanescent wave component and one or more target substances in the medium.

One use of optical devices is in the area of fluorescent immunoassays. Presently, optical waveguides in the form of fiber optic rods typically are coated with either an antibody or an antigen which binds the corresponding antigen or antibody, respectively, suspected of being present in a medium or test sample. This coating typically is applied prior to the performance of an immunoassay measurement. In a "sandwich" immunoassay, an antibody is bound to the surface of the fiber optic rod to form a reactant coating, and the device is subsequently immersed in a sample suspected of containing the antigen to be analyzed. Antigen present in the sample binds with the attached antibody. A second antibody, previously labelled by a fluorescent tag, is added to the sample. Alternatively, in a "one-step" assay, the second, labelled antibody is first mixed with the antigen in the sample, and the mixture is brought into contact with the fiber optic rod and the first, bound antibody. In either technique, the labelled antibody attaches to the antigen to form a tagged complex bound to the fiber optic rod by the first antibody.

Light is subsequently introduced into the fiber optic rod at one or more wavelengths and is propagated along the fiber optic rod by total internal reflection. The reflection is, of course, not completely total since the fluorescent tag absorbs a small amount of the radiation. The attached fluorescent tag (referred to as a fluorophore) absorbs energy from the evanescent wave electromagnetic fields at a first wavelength and fluoresces at a second, longer wavelength. Fluorescence from the excited fluorophore passes into the optical waveguide via a tunneling effect and the portion of the fluorescent radiation which occurs at an angle greater than the critical angle is propagated through the optical waveguide to emerge from an output end.

Several improved dielectric waveguides are described in U.S. Pat. No. 4,880,752; which is incorporated herein by reference. In one construction, the waveguide has an elongated rod-shaped core having an opening within the core material. A reactant coating is disposed about the opening within the core on a single optical surface.

Presently, only a single analyte is analyzed in most conventional procedures. There is, however, a need for analyzing more than one analyte at a time, or for simultaneously examining a reference material to indicate fluctuations in light intensity, defects in the optical surface of the sensor, and similar factors which may alter the amount of fluorescence detected. For example, a variation in diameter of wall thickness of a fiber optic rod changes the angle at which light is totally internally reflected, and may cause the radiation to eventually strike at an angle less than the critical angle, and therefore escape the sensor. Alternatively, if the angle becomes increasingly greater than the critical angle, there will be fewer reflections which reduces the amount of evanescent wave electromagnetic fields which are delivered to the surrounding medium.

A number of immunoassay technique formats are known in the art may be practiced with the sensors of the present invention.

SUMMARY OF THE INVENTION

The evanescent wave sensor of the invention has a waveguide with at least two optical surfaces. Radiation is propagated along the waveguide between the first and second surfaces by total internal reflection. The first surface receives a radiation signal which indicates the presence of a first analyte in a medium and the second surface receives a radiation signal representing one or both of a second analyte and/or a reference. The sequence and number of radiation signals may vary depending on the type of analyses being performed by the sensor and the fluorescent tags employed with the assay. The sensor therefore is capable of detecting one or more analytes in a single medium, detecting simultaneously one or more analytes in two different media, or detecting simultaneously an analyte and a reference. Use of a reference provides an automatic indication of fluctuations in light intensity, defects in the optical surface of the sensor, or other factors which affect the apparent quantity of detected output radiation.

In one embodiment, the waveguide is a hollow core having an inner surface and an outer surface. One of the inner and outer surfaces forms the first wave propagating surface and the other of the inner and outer surfaces forms the second wave propagating surface. Alternatively, the waveguide is a shell having a radiation port at a first end and a base at a second end, and having inner and outer wall surfaces extending between the radiation port and the base to form the first and second wave propagating surfaces. One or both of the first and second surfaces can carry a reactant coating which may include a binding partner of an analyte to be detected. The reactant coating may include an immobilized antibody, antigen, enzyme, nucleic acid, receptor, or other known binding molecules. When used for a fluorescent immunoassay procedure, the waveguide is transmissive to light which can excite fluorescence of fluorescent tag and is transmissive to fluorescent radiation from the fluorescent tag. The sensor may further include a substance or element for isolating the first and second surfaces to prevent contact of a single medium with both surfaces. For example, a gel or a solid substance such as polytetrafluoroethylene-co-hexafluoropprpylene can be disposed about the second surface to prevent the medium containing the first analyte from contacting the second wave propagating surface. Therefore, a sensor according to the invention is useful for detecting one or more components of a first medium, or one or more components from a second medium.

This invention also features a method of assaying analytes by providing an optical waveguide having at least first and second wave propagating surfaces, and contacting the waveguide in the medium to contact at least one of the first and second surfaces. Radiation then is propagated through the waveguide between the first and second surfaces to generate evanescent wave electromagnetic fields at both the first and second surfaces to irradiate the medium, and radiation reentering the waveguide and emitted from it, and is detected to assay the analyte. The radiation can interact with an analyte by absorption or by generation of fluorescent radiation.

OBJECTS OF THE INVENTION

It is among the objects of the invention to provide an improved optical waveguide sensor, apparatus, and method for analyzing at least one medium and, in particular, for conducting fluorescent immunoassays.

Another object of the invention is to provide a sensor having at least two optically independent surfaces which can be illuminated by one or more light input signals.

Yet another object of the invention is to provide such a sensor which enables two independent assays to be conducted using a single waveguide.

A still further object of the invention is to provide such a sensor which can enable comparison of a reference output signal with an analyte output signal to determine fluctuations in light intensity or loss due to surface defects.

Yet another object of the invention is to provide such a sensor which enables a greater acceptable variation of sensor geometry by providing automatic referencing within the waveguide.

It is a further object of the invention to provide such a sensor which provides accurate output signals which are independent of a change in diameter or wall thickness of the sensor.

Yet another object of the invention is to provide a sensor which can provide a reference of excitation radiation without contacting the sample with the reference material.

A still further object of the invention is to provide an improved device for guiding excitation radiation into a sensor according to the invention, and for collecting output radiation.

DESCRIPTION OF THE DRAWINGS

The foregoing and other objects and advantages of the invention will be appreciated more fully from the following further description thereof which reference to the accompanying drawings wherein:

FIG. 2A is a schematic side view of a portion of the sensor of FIG. 1 having a first medium (liquid L) contacted against its outer surface;

FIG. 2B is an enlarged schematic view of total internal reflection of radiation having an angle greater than that of the critical angle (relative to a reference line normal to the surface);

FIG. 2C is a schematic representation of the refraction of radiation entering the sensor;

FIG. 3 is a schematic partial cross-sectional view of a hollow core having different reactant coatings 201 on the inner and outer surfaces for analyzing two media;

FIG. 4 is a schematic partial cross-sectional view of a hollow core having separate reactant coatings for analyzing a single medium;

DESCRIPTION OF THE ILLUSTRATIVE EMBODIMENT

Figure 1:
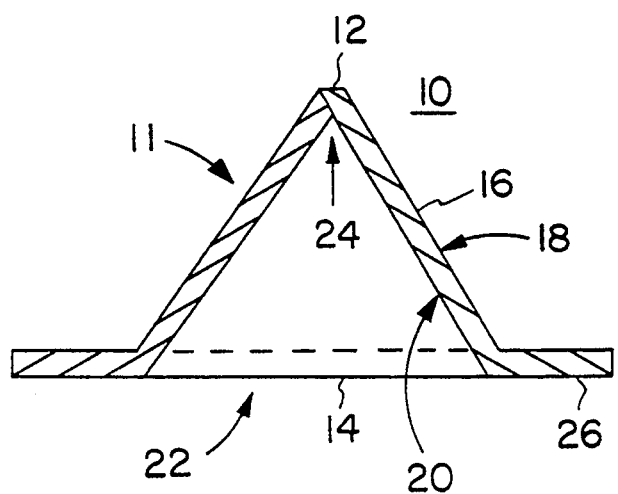
FIG. 1 is a schematic cross-sectional view of a sensor according to this invention configured as a frustoconical shell.

A sensor according to the present invention and method for using the sensor can be accomplished by a waveguide having at least two wave propagating surfaces. The sensor receives a radiation input signal and emits one or more output signals to detect one or more analytes in at least one medium. Analyte, as used herein, shall be understood to include any of a variety of chemical and biochemical substances. The analyte sources may include physiological, scientific and industrial (toxic and nontoxic) test media where the presence, absence or quantity of the analyte in the test medium is sought; and where, for example, the analysis of a physiological analyte is relevant to diagnosis and/or treatment of disease. In one embodiment, the input signal is propagated along the waveguide between the first and second wave propagating surfaces. The first surface is capable of receiving a first radiation signal which indicates the presence of a first analyte, and the second surface is capable of receiving a second radiation signal which represents one or both of a second analyte and a reference. A reactant coating may be disposed on one or both surfaces. A reactant coating as used herein shall be understood to include the attachment by coating means of a molecule which is receptive to a complimentary molecule in a test medium or test sample to form a complex. Coating as used herein shall be understood to include specific and nonspecific reactions including noncovalent binding and covalent binding.

One characteristic of the invention is that the evanescent wave electromagnetic fields generated at the first and second surfaces interact with different substances at the two interfaces between the waveguide and a surrounding medium. (gas, liquid or solid). In one construction, for example, the first wave propagating surface is coated with a binding partner of a first analyte and the second surface is coated with a reference fluorophore. The reactant coating on the first surface binds the first analyte which in turn binds a homologous binding partner carrying a fluorescent tag. The reference fluorophore and the fluorescent tag can be selected so that both are excited by a single excitation wavelength and yet each emits at a different wavelength. The two different emitted fluorescent radiation wavelengths reenter the waveguide and are detected independently to enable accurate determination of the presence or quantity of the first analyte. This configuration and a number of alternative configurations are described in more detail below. Use of the waveguide sensor to analyze more than one media is also described.

There are a number of different constructions of an evanescent wave sensor to provide two or more wave propagating surfaces. One configuration involves a planar plate such as a microscope slide. Another configuration is a hollow core such as described in U.S. Pat. No. 4,880,752, incorporated herein by reference. In yet another configuration, the sensor is a shell having a radiation port at a first end and a base at a second end, with the first and second surfaces extending between the radiation port and the base as described in U.S. patent application S.N. entitled "Evanescent Wave Sensor Shell and Apparatus". One construction of a frustoconical shell is shown as sensor 10, FIG. 1.

Referring to FIG. 1, sensor 10 includes a shell or cone 11, having a planar radiation port 12 and a base 14. A wall 16 extends between the radiation port 12 and the base 14 and defines outer wall surface 18 which forms the first wave propagating surface and inner wall surface 20 which forms the second wave propagating surface. The interior of the shell 11 is hollow and the base 14 defines a circular opening 22 which communicates with the interior. The inner wall 20 converges to a point 24 beneath the radiation port 12 so that virtually all radiation entering through radiation port 12 impinges at a desired angle on inner wall surface 20.

In this construction, the sensor 10 further includes handle 26 which is an annular flange connected to the base 14. In other constructions, a tab or other projection services as a handle. The handle 26 is a non-active surface, and therefore can be grasped without damaging an optically active surface. By comparison, the radiation port 12 and wall surfaces 18 and 20 are optically active surfaces which are optically polished. Both incoming excitation radiation and outgoing fluorescent radiation, of fluorescent compounds known in the art, reflect off the optically polished surfaces 18 and without effect by the handle 26. Radiation which exits through the base 14 or the handle 26 will not affect the assay. Although it is preferred that the handle is integral, it need not be integral but can be a separate member attached to the sensor.

Alternatively, the lower portion of the shell 11 can be designed as a handle and not used as an optically active area. One technique or mechanism for holding a sensor without interfering with the optically active area is disclosed in U.S. Pat. No. 4,671,938 (Cook et al), incorporated herein by reference.

The dimensions of the preferred waveguide sensor 10 are as follows. The radiation port 12 has an outer diameter of 0.92 mm, and the base 14 has an outer diameter of 10.26 mm. The handle 26 has an outer diameter of 16 mm which provides nearly 5 mm of graspable surface along all sides of the shell 11. The sensor 10 is approximately 11.5 mm in length, including a thickness of 0.5 mm for the handle 26. The wall 16 also has a uniform wall thickness of 0.5 mm to provide a large number of internal reflections along its length. The material is polymethyl methacrylate (PMMA) having an index of refraction of 1.4917 at a wavelength of 589.3 nm.

The sensor 10, in comparison to fiber optic rods as used in the art, has a large surface area for its length. For the above-described sensor having a length 11.0 mm exclusive of the thickness of the handle 26, the outer wall surface 18 has an area of approximately 170 $mm^2$. This area is slightly greater than the 157 $mm^2$ of a 50 mm fiber optic rod having a diameter of 1 mm as is presently used in fluorescent immunoassays.

There are several factors to be considered in selecting material for the sensor 10. It is desirable for the material to be injection moldable so that the sensor may be rapidly and inexpensively formed, and easily mass produced. Further, optically polishing the mold establishes optically polished surfaces which do not require further polishing. Another factor is that the material must have an index of refraction greater than that of the intended medium to be analyzed, as described below. Additionally, it is desirable for the material to be optically pure and provide low attenuation of the radiation of interest. Silica glass is suitable for ultraviolet or visible radiation, plastics such as polymethylmethacrylate (PMMA), polystyrene, and polycarbonate are suitable for visible radiation, and fluoride glass or chalcogenide are suitable for near infrared radiation. Other organic polymeric materials such as silicones, acrylates, fluoroacrylates, and the like can also be used as the sensor material. It is also desirable for the material to be nonfluorescent to the radiation of interest for assays involving fluorescence.

Additionally, it is desirable for the material to have suitable surface properties for binding of a reactant coating to it, or to be amendable to modification to assist bonding. PMMA is preferred not only for its optical purity and its injection molding characteristics, but also because it is hydrophobic which enables antibodies and other proteins to be attached to the surface simply by bringing them in contact with the PMMA. For glass, it is desirable to add a silane coating to provide either a hydrophobic surface or one amendable to covalent coupling chemistries.

The shell 10 has an angle a as shown in FIG. 2A. The angle a represents the inclination of the axis of propagation 32 relative to the cone axis 30 which passes through the center of the radiation port 12 and the base 14. The axis of propagation 32 passes through the center of wall 16, halfway between outer wall surface 18 and inner wall surface 20 which are parallel to each other relative to the angle of propagation. The inclination of outer and inner wall surfaces 18, 20 and the cone axis 30 is also angle a.

Light ray 34 is shown propagating through the wall 16 after passing through the port 12, and bouncing between inner wall surface 20 and other wall surface 18 due to total internal reflection. Total internal reflection occurs when the angle of the ray 34 is greater than the critical angle, which in turn depends upon the index of refraction $n_1$ of the wall 16 relative to the index of refraction $n_2$ of a first medium, typically air, through which radiation passes to enter and exit the radiation port 12, and the index of refraction $n_3$ of a second medium, typically a liquid L, which surrounds a lower portion of the sensor 10 and contacts only the outer surface 18 as illustrated, or contacts both outer surface 18 and inner surface 20 as described below. In the construction shown in FIG. 2A, air surrounds the remainder of the shell 11 including radiation port 12 and all of the inner wall surface 20. The relative indices of refraction, the calculation of the critical angle, and the desired angle of radiation entering and propagating through the sensor are described in more detail below.

In this construction, the liquid L is contacted to a portion of the outer wall 18, which is coated with a reactant coating 36 which may be an immobilized antibody, an antigen, a receptor, a nucleic acid, an enzyme, or other binding substances as is known in the art. It is desirable for the reactant coating to bind an analyte suspected of being present in the medium. The inner wall surface 20 is coated with a reference fluorophore 37 such as a binding substance labelled with a fluorescent dye.

To prepare a waveguide sensor formed of PMMA for use in a sandwich immunoassay, a first antibody is attached or coated to the outer surface 18 and a reference fluorophore is attached to the inner surface 20 by separate dip-coating steps after the surfaces 18, 20 are suitably cleaned. One technique for cleaning the surfaces 18, 20 is by sonicating the sensor for several seconds while it is immersed in a Freon TF bath.

The first antibody, attached to the outer surface 18, forms a complex when a first analyte in the liquid L contacts the first antibody. A typical antibody has a height of approximately 100 angstroms (A), and binds an antigen having a typical thickness of 100–200 A in the case of a large molecular weight antigen. A second antibody having an attached fluorophore is then contacted against the antigen to form a tagged complex having a fluorophore spaced approximately 300–400 A from the outer wall surface 18. When a light ray 34 bounces against the surface of the wall 18, as shown for point 38, an evanescent wave excites the fluorophore which induces emission at a longer wavelength. The fluorescent emission is indicated by rays 40, shown in phantom. The portion of the rays 40 which are internally reflected are propagated back through the radiation port 12 and detected as described below. This portion depends strongly on he distance of the fluorophore from the PMMA/media interface, and decreases rapidly with increasing distance as expected for a tunneling-like effect. Similarly, when light ray 34 bounces against the inner surface 20, as shown for point 39, an evanescent wave excites the reference fluorophore 37 which induces emission at a different wavelength, as indicated by rays 41, shown in phantom. Both fluorescent radiation 40 from the reactant coating 36 and the fluorescent radiation 41 from the reference fluorophore 37 are shown exiting from the radiation port 12 for subsequent detection.

The parameters of a particular cone construction are as follows. The critical angle c relative to reference line RL, FIG. 2B, is calculated according to the formula:

$$c = \sin^{-1}(n_2/n_1)$$

where $n_1$ is the index of refraction of the shell and $n_2$ is the index of refraction of the first medium (air) contacting the interior of the shell. When the index of refraction $n_3$ of the second medium (the sample to be analyzed) is greater than $n_2$, then $n_3$ is used as described below. In this construction the reference fluorophore 37 is sufficiently thin so that it does not significantly alter the index of refraction of the surrounding air.

Radiation having an angle greater than that of angle c, such as angle b of ray 42, will be totally internally reflected as shown by ray 42a. A plastic material such as PMMA has an index of refraction $n_D$ of approximately 1.49 and fused silica has index of refraction of approximately 1.46. For the media surrounding the sensor, air has an index of refraction of approximately 1.00, whereas many biological liquids have an index of refraction of approximately 1.33. For analysis of such liquids, it is therefore desirable for the sensor to have an index of refraction of greater than 1.33. Likewise for the analysis of solid coatings, the sensor material index ($n_1$) must be greater than index $n_3$ or that associated with a solid coating of interest. By way of example, a polystyrene waveguide sensor having $n_D = 1.59$ may be utilized in evanescent wave interrogation of methyl cellulose ($n_D = 1.49$) or natural rubber ($N_D = 1.52$) polymeric coatings.

Alternatively, the sample to be analyzed may be contained in a gas or a liquid phase which is exposed to a solid composite construction. For example, a solid silicone containing a fluorescent material such as a ruthenium-based dye is coated onto the outer surface of a PMMA sensor as a layer having a thickness of 1–10 microns. The sensor is then exposed to another medium such as blood or gas, and the oxygen contained therein diffusing into the silicone layer quenches (reduces) the fluorescence of the dye. The amount of quenching affects the level of detected fluorescence. Silicone has an index of refraction of approximately 1.43, and therefore the sensor substrate in this application requires an index of refraction greater than 1.43 for waveguiding and evanescent pumping of the silicone layer. In this case the evanescent wave does not propagate into the gas or blood sample, rather the interaction is confined to a fraction of a wavelength depth into the silicone coating layer. In other words, the reactant coating has a low refractive index and a sufficient thickness so as to preclude direct interaction of light between the sensor and the medium to be analyzed. The critical angle c would thus be calculated to be $\sin^{-1}(1.43/1.49) = 73.7°$) for dye-doped silicone and PMMA. It is to be noted that a reactant coating typically is sufficiently thin so that it does not noticeably refract radiation passing through it, especially when the reactant coating is in a fully hydrated state. Otherwise, the effect of the reactant coating must be accounted for.

Because the critical angle is greater at the interface of the sensor and the liquid L than that of the sensor-air interface, in the case of a liquid based sensor, the critical angle defined by the sensor substrate and the measured liquid L is used to establish the minimum acceptable angle of a ray 42. For example, where the fluid to be analyzed is a liquid having an index of refraction $n_D$ of 1.33 and the sensor is formed of PMMA having index of refraction $n_D$ of 1.49 at a wavelength of 589.3 nm, the critical angle is 63.2°. To allow a deviation in angle of up to 3.8°, angle b is selected to be 67°. Subtracting this angle from 90° establishes angle a as 23°.

Next, an acceptable launch angle e is calculated as shown in FIG. 2C. A light ray 44 has an angle of refraction d according to Snell's Law:

$$n_2 \sin e = n_1 \sin d$$

If angle d is allowed to be as large as 3.8°, angle e is 5.6°.

In summary, the cone is constructed by selecting the index of refraction of the cone material and the medium to be analyzed, and determining the critical angle at the interface of the cone and the medium for wave guiding of radiation at the desired wavelength. The cone angle is calculated with respect to the axis of propagation by subtracting the critical angle from 90°. For a collimated radiation source, this angle may, in principle, be used. However, in practice, the one apex angle is made somewhat less to account for misalignments and mechanical tolerances. If there is an angle of incidence at the radiation port 12 of greater than 0°, the cone apex angle is reduced to make the walls steeper. The length of the cone is selected to provide the required surface area. It is desirable to form the walls of the shell as thin as possible to increase the number of bounces between the outer and inner wall surfaces, and it is desirable for the radiation introduced into the cone to be as close to the critical angle as possible, but still within the waveguiding angle(s), to maximize the evanescent wave component delivered to the interface of the shell and the medium.

A number of different techniques for using two or more wave propagating surfaces of a single waveguide are illustrated in FIGS. 3–9 for analyzing one or more media. The waveguide is a hollow core such as described in U.S. Pat. No. 4,880,752. Referring to FIG. 3, sensor 200 analyzes two media simultaneously and includes a first reactant coating 202 disposed on an outer surface 204 and a second reactant coating 206 disposed on an inner surface 208. The first reactant coating 202 includes a first antibody 210 which is the binding partner of a first analyte 212, and the second reactant coating 206 includes second antibody 214 which is specific for second analyte 216. The analytes 212, 216 are present in two separate liquids $L_1$ and $L_2$, respectively. In one example of this embodiment, the first antibody 210 is anti-CKMM (anti-creatine kinase having two muscle subunits) and the second antibody 214 is anti-CKMB (anti-creatine kinase having a muscle subunit and a brain subunit).

The first and second reactant coatings 202, 206 are established on surfaces 204, 208, respectively, after the surfaces are cleaned such as by sonication in a Freon bath as described above. No further preparation of the surface is required if the waveguide is formed of PMMA. If the material is a silica glass, the surface is prepared by silanization such as described in U.S. Pat. No. 3,652,761. The opening leading to the inside of the waveguide 201 is plugged and the waveguide 201 is dipped into a solution containing the first antibody 210. The waveguide 201 is removed from the first solution, rinsed if necessary, and its ends unplugged. A second solution is prepared containing the second antibody 214, into which the waveguide 201 is immersed to coat the inner surface 208. The second antibody 214 does not bind to the outer surface 204 because that surface is effectively blocked by the previously applied first antibody 210.

During use, the first liquid $L_1$ is contacted with the first reactant coating 202 and the second liquid $L_2$ is contacted with the second reactant coating 206. In one construction, a reservoir is established about the outer coating 204 to contain the first liquid $L_1$, and the second liquid $L_2$ is drawn inside the sensor 200 by capillary action from a second reservoir. The first analyte 212 attaches to the binding site of the first bound antibody 210, and a corresponding antibody 220 labelled with a first fluorescent tag 222 binds with the first antigen 212 in solution or after the antigen 212 is bound by the reactant coating 202, depending whether the assay is a one-step or two-step procedure. Simultaneously, the second analyte 216 binds with a corresponding antibody 224 labelled with a fluorescent tag 226 and binds with a second reactant coating 206. Thereafter, radiation 228 propagated along the waveguide 201 generates evanescent wave electromagnetic fields which stimulate the first fluorescent tag 222 and the second fluorescent tag 226. A single excitation wavelength, for example, at 480 nm, can stimulate two different dyes such as BPE (B-phycoerythrin) and fluorocein. BPE emits radiation having an emission maximum at approximately 575 nm as described for example in U.S. Pat. No. 4,520,110 and U.S. Pat. No. 4,542,104 and fluorocein emits most strongly at approximately 520 nm. The two different emitted fluorescent radiation wavelengths can be detected separately as described in more detail below. The first fluorescent tag 222 is shown emitting radiation 230, some of which reenters the waveguide 201 for detection, and the second fluorescent tag 226 emits radiation 232, a portion of which also reenters the waveguide 201 for detection as described below.

A sensor 240, FIG. 4, contains a first reactant coating 202 and a second reactant coating 206 as described above for FIG. 3, but both reactant coatings are exposed to the same liquid $L_3$. In this manner, two analytes in a single fluid are assayed.

Figure 5:
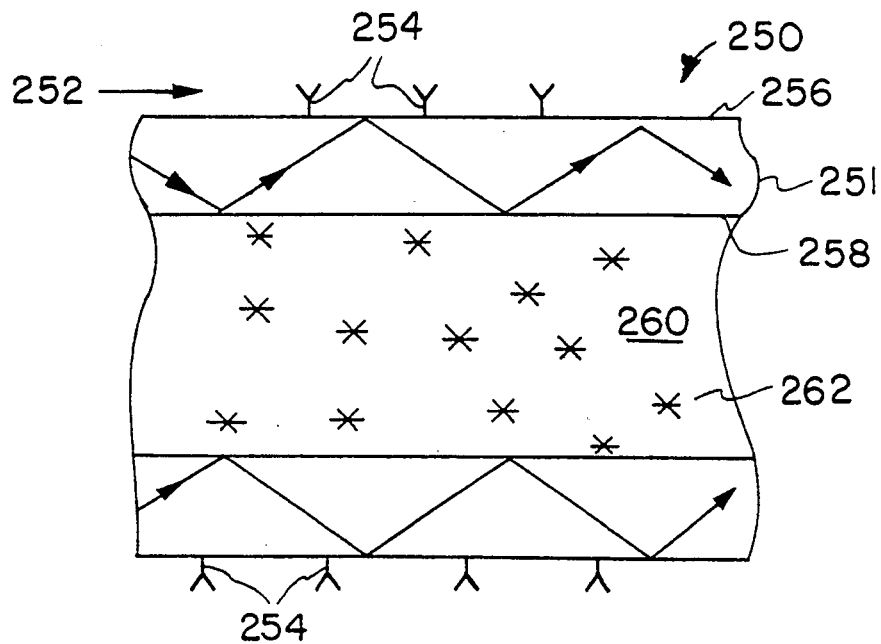
FIG. 5 is a schematic, partial, cross-sectional view of a hollow core in which the inside of the rod is filled with a gel containing a reference fluorophore.
Figure 6:
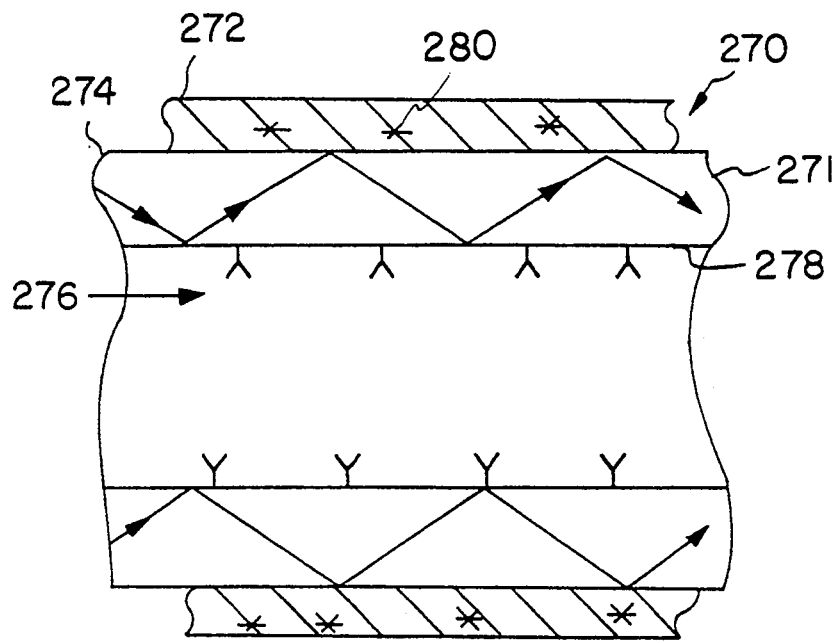
FIG. 6 is a schematic partial cross-sectional view of a hollow core having a solid coating covering the outer surface and containing a reference fluorophore. Additionally, the solid coating 272 provides a handle for manipulation of the sensor 270 without marring an optical surface.

Two additional embodiments of the waveguide sensors according to the invention having optical surfaces exposed to different media are shown in FIGS. 5 and 6. Referring to FIG. 5, sensor 250 includes first reactant coating 252 including a first antibody 254 attached hydrophobically to the outer surface 256. Inner surface 258 is contacted with an agarose gel 260 containing a fluorescent dye 262 such as FITC (fluorescein isothiocyanate). The sensor 250 is prepared by drawing the gel 260 in liquid form into the waveguide 251. The gel 260 is allowed to cool and solidify. When FITC is used as the reference dye 262, its typical concentration is approximately $5 \times 10^{-8}$ M. The waveguide 251 is thereafter dip-coated with the antibody 254 to establish the first reactant coating 252. Dye 262 serves as a reference which indicates the actual excitation radiation delivered to fluorescent tags bound to the first reactant coating 252.

By comparison, the sensor 270, FIG. 6, includes a reference media 272 covering its outer surface 274 and carries a first reactant coating 276 on its inner surface 278. The media 272 in one embodiment is a solid coating formed of FEP (polytetrafluoroethylene-co-hexafluoropropylene) having an index of refraction of $n_D = 1.338$. The FEP is doped with a fluorescent dye 280 such as ruthenium (tris2,2'-bypyridiyl ruthenium II dichloride) and forms a layer approximately 10 microns of thickness. The FEP layer is applied to the outer surface 274 after the ends of the waveguide 271 are capped. The ends are then decapped and the waveguide 271 is dip-coated with the antibody 276.

Figure 7:
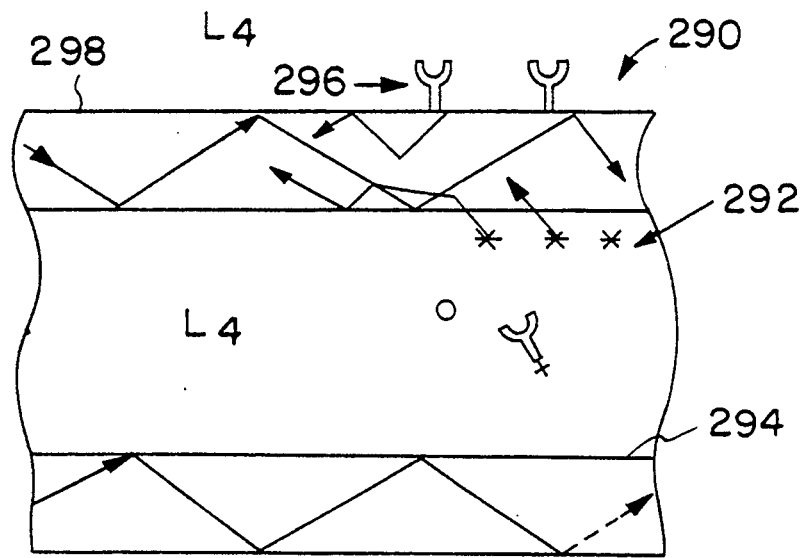
FIG. 7 is a schematic partial cross-sectional view of a hollow core having a reactant coating disposed about its outer surface and a reference fluorophore attached to the inner surface for analyzing a single medium.

Sensor 290, FIG. 7, includes a reference 292 attached to inner surface 294 and a first reactant coating 296 attached to outer surface 298. The sensor 290 is useful for analyzing a single medium $L_4$ when it is not necessary to isolate the reference dye 292 from the medium being analyzed. Comparison, sensor 250, FIG. 5, and sensor 270, FIG. 6, isolate the reference dyes from the medium being analyzed. In contrast, sensor 250, FIG. 5, and sensor 270, FIG. 6, isolate the reference dyes from the medium being analyzed.

Figure 8:
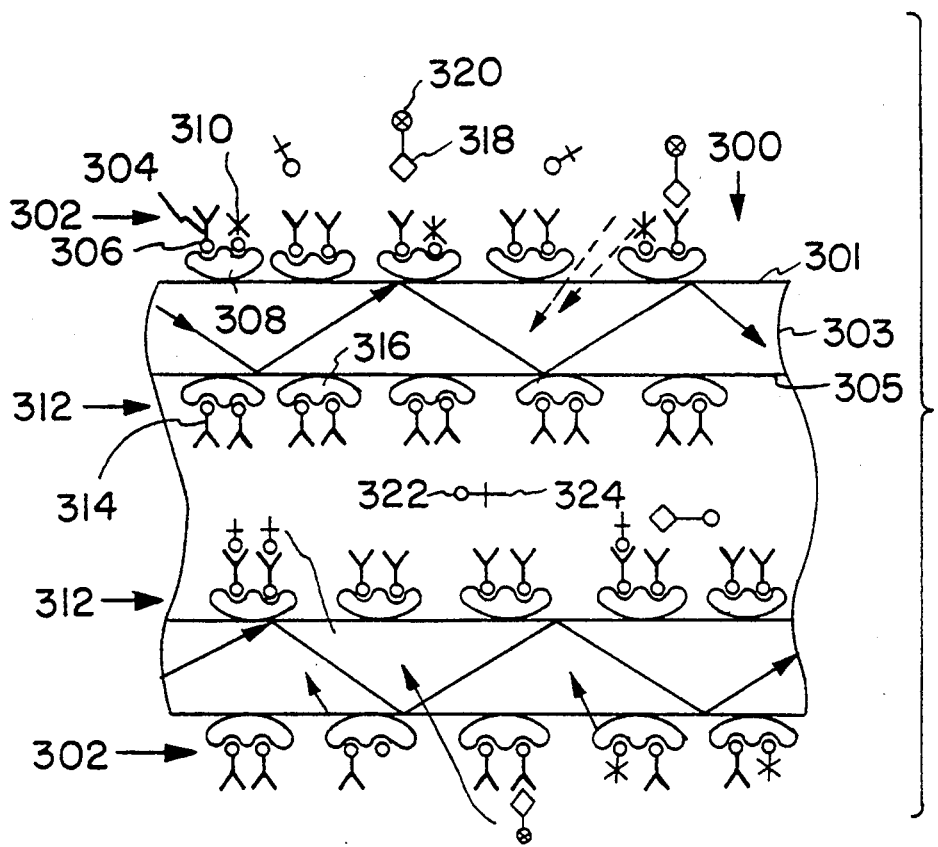
FIG. 8 is a schematic partial cross-sectional view of a hollow core having two surfaces coated with avidin to bind a first antibody and a reference to the outer surface and a second antibody to the inner surface.

Sensor 300, FIG. 8, assays two analytes in a medium and simultaneously provides a reference. Additionally, both surfaces are coated with avidin to provide initial binding surfaces 308 and 316. The first reactant coating 302 includes a first antibody 304 which is biotinylated, that is, a biotin molecule 306 is attached to the antibody 304 to enable binding with the avidin 308. The first coating 302 also contains a biotinylated reference dye 310, such as fluorescein. A second coating 312 includes second antibody 314 which is biotinylated to bind with the avidin 316. Alternative binding molecules/pairs are well known in the art and may be utilized with the sensors of the present invention depending in part on the analytes sought to be detected.

The first antibody 304 binds with first analyte 318 which is labelled with a fluorescent tag 320. The second antibody 314 binds a second analyte 322 carrying a fluorescent tag 324. In one embodiment, the first antibody 304 is anti-CKMM and the second antibody 314 is anti-CKMB. The first tag 320 is Texas Red ® and the second tag 324 is BPE.

The sensor 300 is formed by coating both inner surface 305 and outer surface 301 with the avidin 308, 316 binding surfaces, or streptavidin, which is in solution at a concentration of approximately 200 micrograms per milliliter. Both openings to waveguide 303 are capped, and the waveguide 303 is dip-coated in a dilute solution of biotinylated fluorocein 310. The sensor then is dip-coated in biotinylated anti-CKMM, at a concentration of approximately 50-200 micrograms per milliliter to occupy the remaining binding sites of the outer avidin coating 308. The ends of the waveguide 303 is dip-coated in biotinylated anti-CKMB to establish the second reactant coating 312.

The use of fluorophores which emit at two or more different wavelengths and the detection of two or more output wavelengths is the subject of U.S. patent application Ser. No. 07/712,304 entitled "Multiple Output Referencing System for Evanescent Wave Sensor", incorporated herein by reference. When fluorescent 320 is TEXAS RED ® fluorescent dye (trademark of Molecular Probes, Inc., Eugene, OR) and the reference dye 310 is fluorecein, two peak emission wavelengths can be detected at 615 nm and 520 nm, respectively. In the use of two or more services according to the present invention, a third output wavelength at 576 nm can be detected when the second fluorescent tag 324 is BPE.

Figure 9:
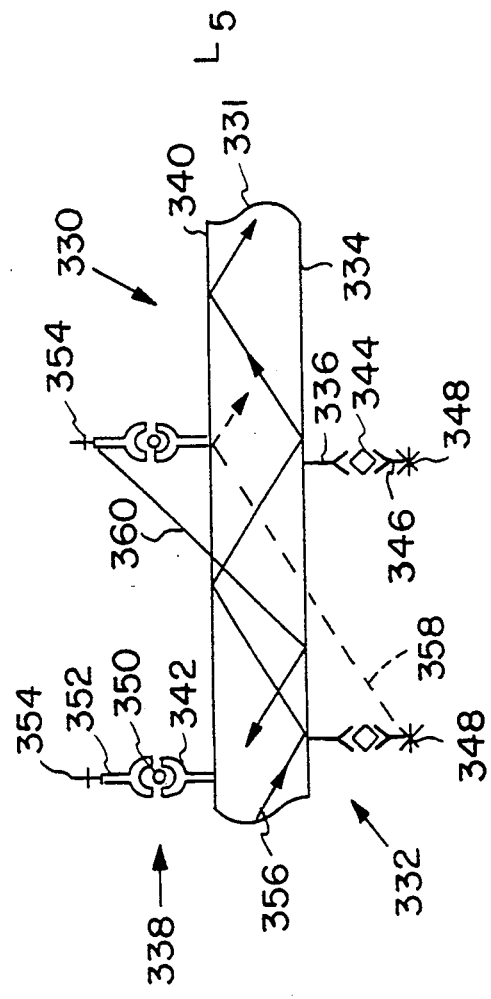
FIG. 9 is a schematic partial cross-sectional view of planar waveguide having fluorophores which transfer energy across the waveguide.

Sensor 330, FIG. 9, illustrates energy transfer across two optical surfaces according to another embodiment of the invention to provide a correlated assay. The waveguide 331 is formed as a planar element such as a microscope slide. The first reactant coating 332 attached to first surface 334 includes attached first antibody 336 such as anti-CKMM, and second reactant coating 338 attached to second surface 340. The second reactant coating 338 includes attached antibody 342 such as anti-CKMB. In this embodiment, the attached anti-CKMM antibody 336 binds CKMM antigen 344 which in turn binds taqged anti-CKMM antibody 346 having fluorophore 348 such as RPE (R-phycoerythrin). The anti-CKMB second antibody 342 binds with a CKMB second antigen 350 which in turn binds anti-CKMB antibody 352 with fluorescent tag 354 such as APC (allophycocyanin).

During use, the sensor 330 is immersed in a liquid $L_5$ suspected to contain both CKMM antigen 334 and CKMB antigen 350. Blue excitation radiation 356 at approximately 485 nm is propagated between the first and second surfaces 334 and 340. Green light is emitted at approximately 576 nm from the RPE dye 348 only when the CKMM antigen 344 is present. The bound RPE dye 348 is excited by the evanescent wave electromagnetic fields and emits green light 358 which reenters the waveguide 331 and produces additional evanescent wave effects. The effects excite the APC dye 354 which emits red light 360 at a wavelength of approximately 660 nm. The ratio of green to red light can be used to determine the relevant amounts of CKMM antigen to CKMB antigen, or simply the red wavelength 360 can be monitored to confirm the presence of both antigens. In an alternative embodiment, the second coating 338 is a nonreactive coating containing APC. The APC dye will be stimulated only if CKMM antigen is present, because the RPE dye 348 must be present in order the excite the APC. When a known amount of APC is used, the ratio of green to red light provides an indication of the actual amount of CKMM antigen present in the liquid $L_5$.

Figure 10A:
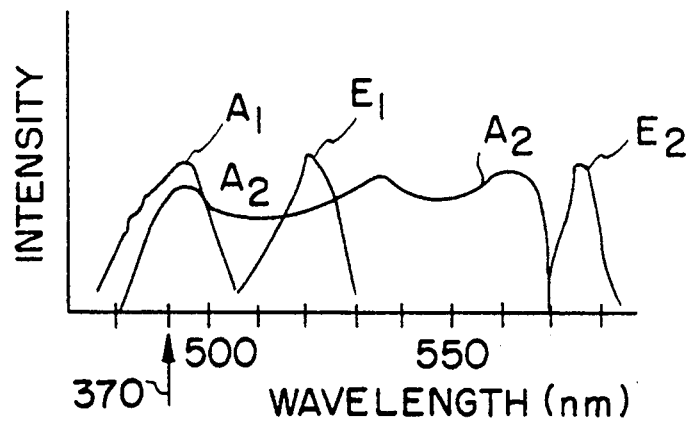
FIG. 10A is a chart of intensity versus wavelength showing overlapping absorption or excitation wavelengths and two different emission wavelengths.
Figure 10B:
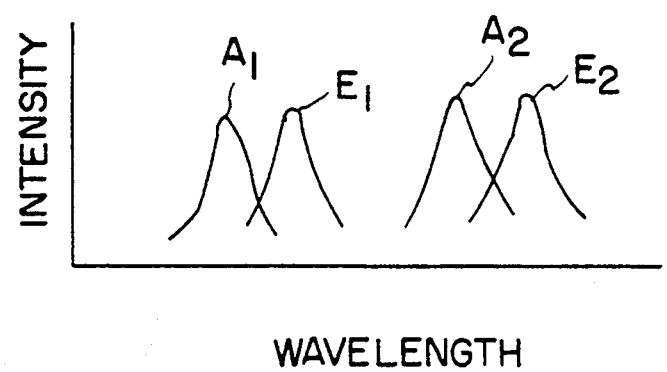
FIG. 10B is a chart showing two fluorophores having different absorption and emission spectra.
Figure 10C:
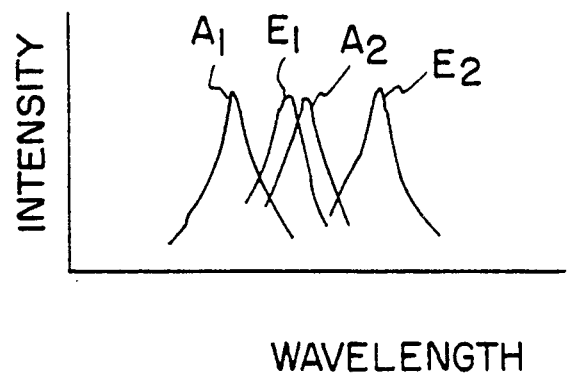
FIG. 10C is a chart showing overlapping spectra of the emission wavelength of a first fluorophore and the absorption wavelength of a second fluorophore.

Use of different fluorophores having selected absorption and emission spectra are illustrated in FIGS. 10A-10C. The chart of FIG. 10A illustrates two fluorophores which have overlapping absorption spectra $A_1$ $A_2$, such as for the dyes FITC and BPE. Both fluorophores can therefore be stimulated by a single excitation wavelength, indicated by arrow 370 between 500-505 nm. The FITC has an emission spectra $E_1$ which is different from emission spectra $E_2$ of BPE, and therefore two different output signals are generated.

The use of two fluorophores having different absorption and emission spectra is illustrated in FIG. 10B. Neither the absorption spectra $A_1$ nor the emission spectra $E_1$ overlap with the second absorption spectra $A_2$ or the emission spectra $E_2$ of the second fluorophore. In one example, the first fluorophore is FITC and the second fluorophore is Texas Red ® fluorescent dye.

The use of two fluorophores in which the emission spectra $E_1$ overlaps the absorption spectra $A_2$ of the second fluorophore is illustrated in FIG. 10C. One such set of dyes is DPE and APC as described above for FIG. 9. Other combinations include BPE and Texas Red ® fluorescent dye or fluorocein.

Therefore, it can be seen that a number of dye combinations can be used with the present invention in the use of two or more optical surfaces. A partial listing of suitable dyes is illustrated below in TABLE I.

TABLE I

| ABBR | DYE | APPROXIMATE ($\cong 50\%$) Abs RANGE nm | EXCITATION WAVELENGTH max nm | EMISSION WAVELENGTH max nm |
|---|---|---|---|---|
| FITC | Fluorescein isothiocyanate | 475–505 | 493 | 520 |
|  | Fluorescein | 475–505 | 496 | 520 |
| RPE | R-Phycoerythrin | 480–570 | 495, 536 | 576 |
| BPE | B-Phycoerythrin | 500–570 | 546 | 576 |
|  | rhodamine B | 500–585 | 578 | 604 |
| TR | Texas Red ® | 580–610 | 596 | 615 |
| CPC | C-phycocyanin | 570–640 | 620 | 650 |
| APC | Allophycocyanin | 600–660 | 650 | 660 |
| RPC | R-phycocyanin | 545–635 | 555, 618 | 642 |
| RUTHENIUM | Tris (2,2'-bipyridiyl) ruthenium II dichloride | 410–490 | 450 | 610 |

It will also be apparent from the foregoing that a sensor according to the invention can be implemented using a cone, hollow rod, a planar element, or other waveguide which presents two or more different optical surfaces. Further, although the monitoring of one or more different wavelengths of fluorescent emission radiation is described, other effects such as absorption can be used instead or in combination with the above.

Figure 12:
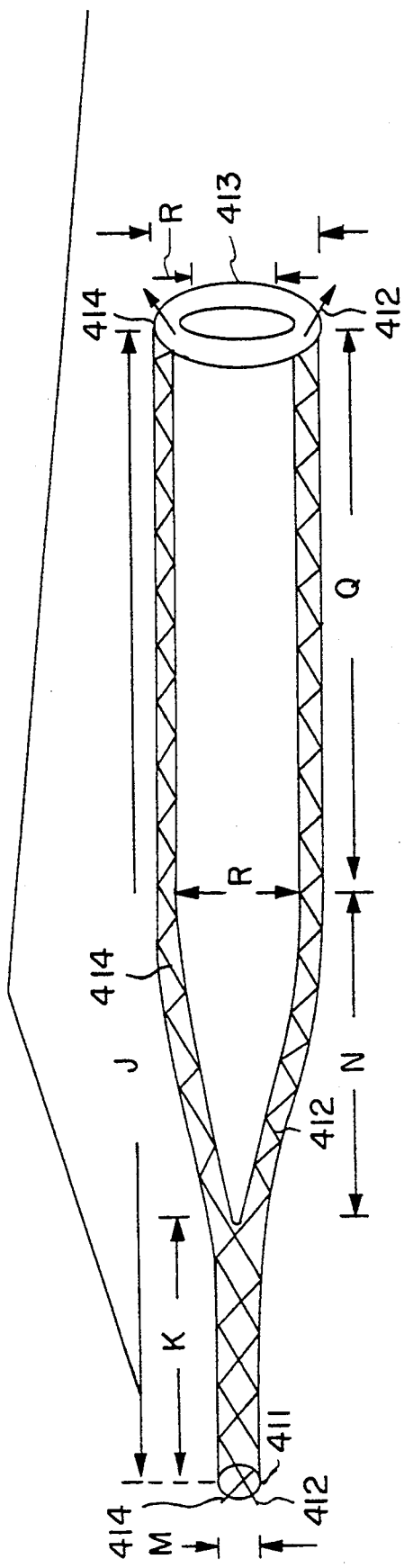
FIG. 12 is a schematic cross-sectional view of an alternative launcher for delivering light to a hollow core.
Figure 11A:
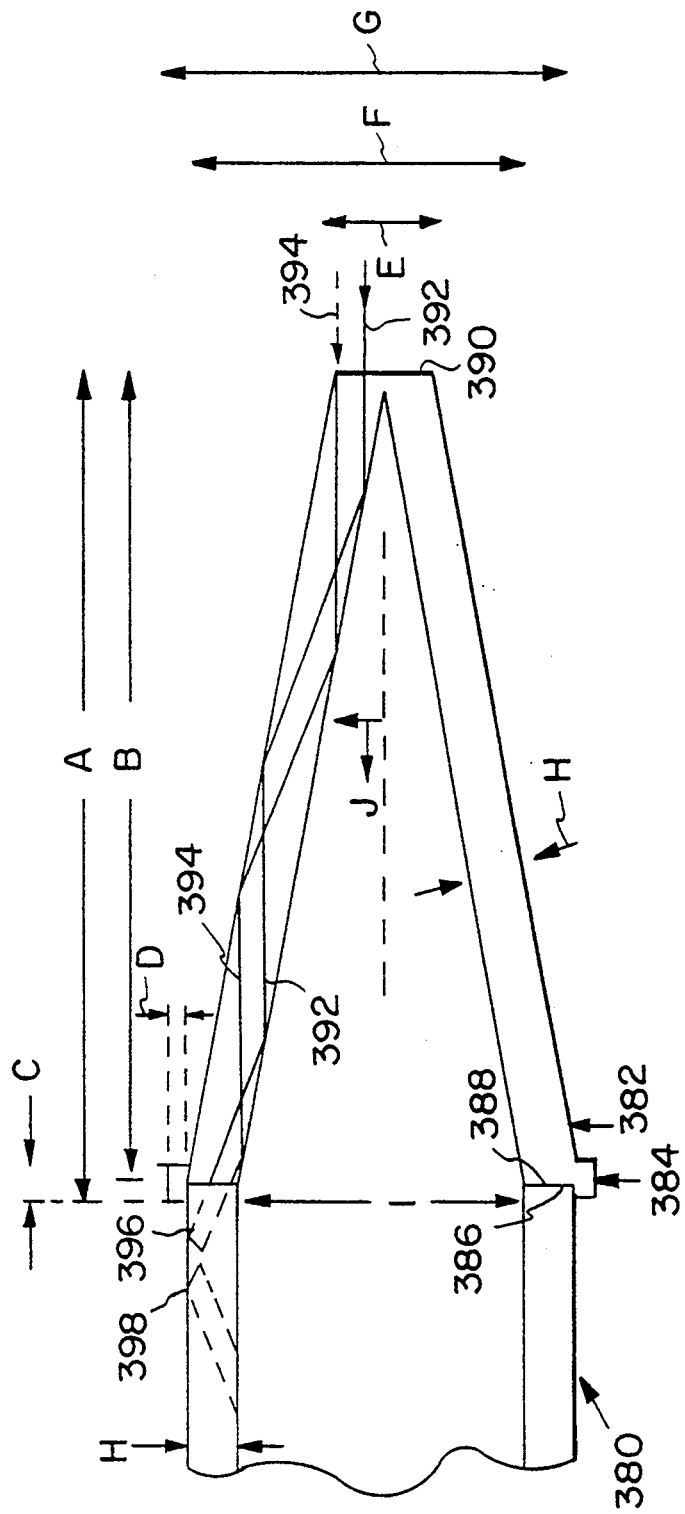
FIG. 11A is a schematic partial cross-sectional view of a cone used as a launcher to deliver light to an end of the hollow core.
Figure 11B:
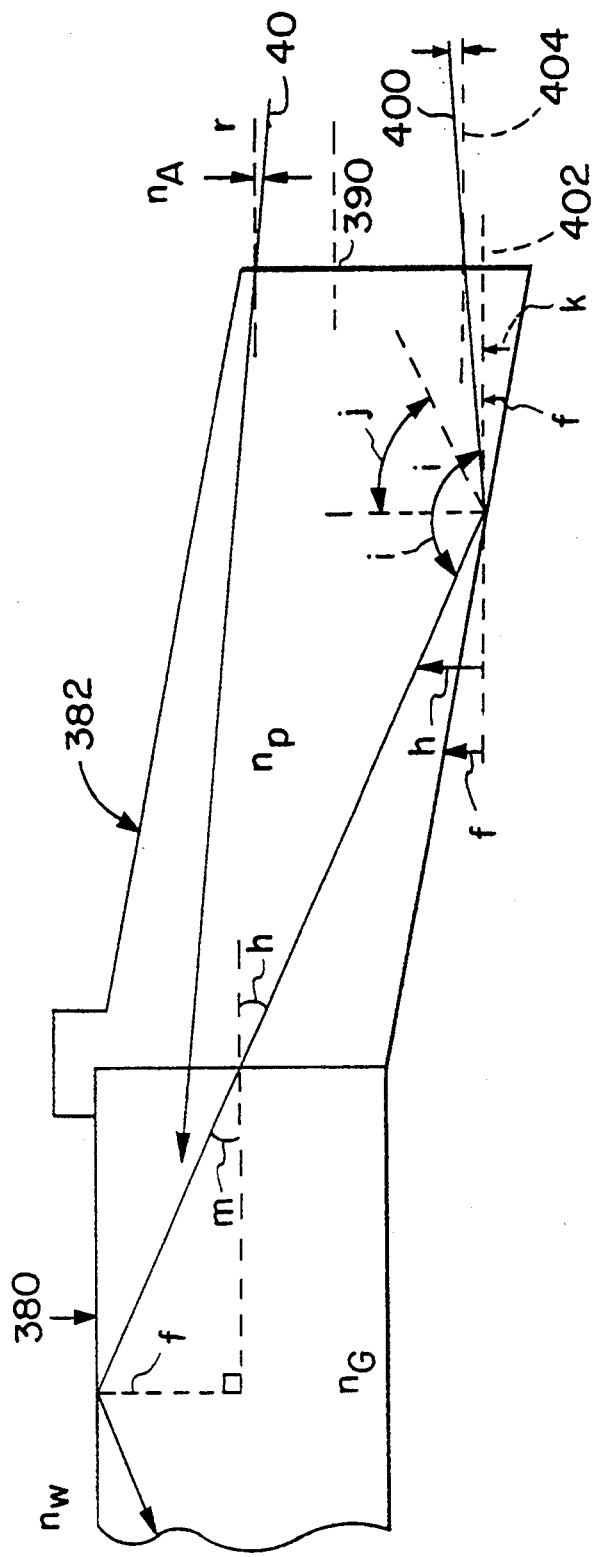
FIG. 11B is an enlarged schematic view of a portion of the device of FIG. 10A illustrating the reflection of a propagated light ray.

Two different devices for delivering light into a hollow rod are shown in FIGS. 11A–11B and FIG. 12, respectively. The hollow rod 380, FIG. 11A, is combined with a conical launcher 382 which is similar to the conical sensor described in the cross-referenced patent application, "Evanescent Wave Sensorship and Apparatus". The launcher 382 includes an annular flange 384 which press-fits around the outside of the rod 380 to butt-couple the edge 386 of the rod 380 with the edge 388 of the launcher 382. If more secure attachment is desired, a nonfluorescent epoxy may be used to join surfaces 386, 388 such as Epo-Tek ® 301 epoxy available from Epoxy Technology, Inc., Billerica, Massachusetts. The Epo-Tek ® 301 epoxy is acceptable when the launcher 382 is formed of PMMA and the rod 380 is formed of silica glass.

Acceptable dimensions of the launcher 382 are as follows when the rod 380 has an inner diameter I of 1.5 mm, an outer diameter F of 2.0 mm, and a wall thickness H of 0.25 mm. The launcher 282 has an overall length A of 4.45 mm and an effective length B of 4.25 mm. The overall length A includes length C of 0.2 mm for the flange 384. The thickness D of the flange 384 is 0.1 mm. Therefore, the launcher 382 has an overall diameter G of 2.2 mm and an effective diameter F of 2.0 mm. The radiation port 390 has a diameter E of 0.5 mm. Although the radiation port 390 is shown as planar, a convex or concave surface may instead be used to focus or defocus incoming radiation, respectively. The launcher 382 has a cone angle f of 10°. The launcher 382 has a thickness H of 0.25 mm, the same as that of the hollow rod 380.

The path of light rays introduced at different positions on the radiation port 390 is illustrated by rays 392, 394. The ray 392 is first reflected from the outer surface of the hollow rod 380 at location 396 and the ray 394 is first reflected at location 398, thereby generating evanescent wave electromagnetic fields. It is desirable to generate as many internal reflections as possible so that a maximum amount of the evanescent wave electromagnetic fields are generated.

Calculation of the angles of the launcher 382 and the radiation introduced into it is shown schematically in FIG. 11B. First, the indeces of refraction $n_D$ for the launcher 382, the sensor 380, the air or other medium between the light source and the radiation port 390, and the medium to be analyzed The index of refraction $n_A$ of air is 1.0002, the index $n_W$ for water is 1.3333, the index $n_G$ of the silica glass sensor 380 is 1.4584, and the index $n_P$ of the PMMA launcher 382 is 1.4917. The object of the design is to produce an angle q which is equal to or greater than the critical angle established between the sensor 380 and the medium to be analyzed. The critical angle q is calculated according to the formula.

$$q = \sin^{-1}(n_W/n_G) \qquad 1$$

In this example, the critical angle q is calculated to be 66.095°. The entrance angle m is determined by subtracting the angle q from 90° and in this example is 23.904°. Similarly, the critical angle j for the launcher 382 is calculated according to equation number 1 to be 42.106°. The actual angle of incidence i of the light ray 400 must therefore be greater than or equal to 42.106°. The incident angle h is calculated according to Snell's Law:

$$n_P \sin h = n_G \sin m \qquad 2$$

In this example, the incident angle h equals 23.338°.
The cone angle f is determined by identities:

$$h - f + i = 90° \qquad 3$$

and $$i + k + f = 90° \qquad 4$$

therefore $$h - 2f = k \qquad 5$$

In this example, angles f and k are measured relative to reference line 402 which is perpendicular to the radiation port 390. The incoming light angle 1 is measured relative to the reference line 404 which is also perpendicular to the radiation port 390.

For light approaching the radiation port 390 at an angle 1 equals 0, angle k equals 0, and angle f is less than or equal to ½ angle h. Angle f in this example is therefore less than or equal to 11.669°.

If the launcher angle f is selected to be 10°, then angle k is 3.338°. Angle 1 is calculated according to the formula:

$$n_A \sin 1 = n_P \sin k \qquad 6$$

For the above values, the incident angle 1 is 4.981° and angle i is determined according to equation number 3 to be 76.662°.

The cone angle f directly effects the incident angle 1. As angle f decreases, angle 1 increases.

The light ray 406 illustrates a path taken by radiation entering the radiation port 390 near its outer edge and at an angle 1 which is the opposite to that of ray 400. The path of ray 406 is undesirable because it inters the sensor 380 at a very large angle relative to the critical angle and therefore will have very few internal reflections. Therefore, it is desirable to have most of the light delivered at angle h.

An alternative launcher 410 is shown in FIG. 12. The launcher 410 is heated and drawn from a borosilicate microcapillary tube having an outer diameter of 1.5 mm and an inner diameter 1.15 mm. During drawing, the inner and outer surfaces of the launcher 410 are maintained approximately parallel to each other. These dimensions correspond to inner diameter R, outer diameter S which applied to length Q, which is 25.5 mm in this example. The launcher 410 has a tapered portion having a length N of 7 mm and a fully reduced diameter portion of a length K of 6.5 mm. The final diameter of radiation port 411 is 0.762 mm.

During use, the exit port 413 of the launcher 410 is butt-coupled with a 1.5 mm outer diameter borosilicate capillary tube which serves as a sensor according to the present invention. The paths of two rays 412, 414 are illustrated schematically. Excitation radiation is introduced through the radiation port 411 at the same angle as if the radiation were introduced directly into the sensor. The overall length J of sensor 410 is approximately 39 mm.

Figure 13:
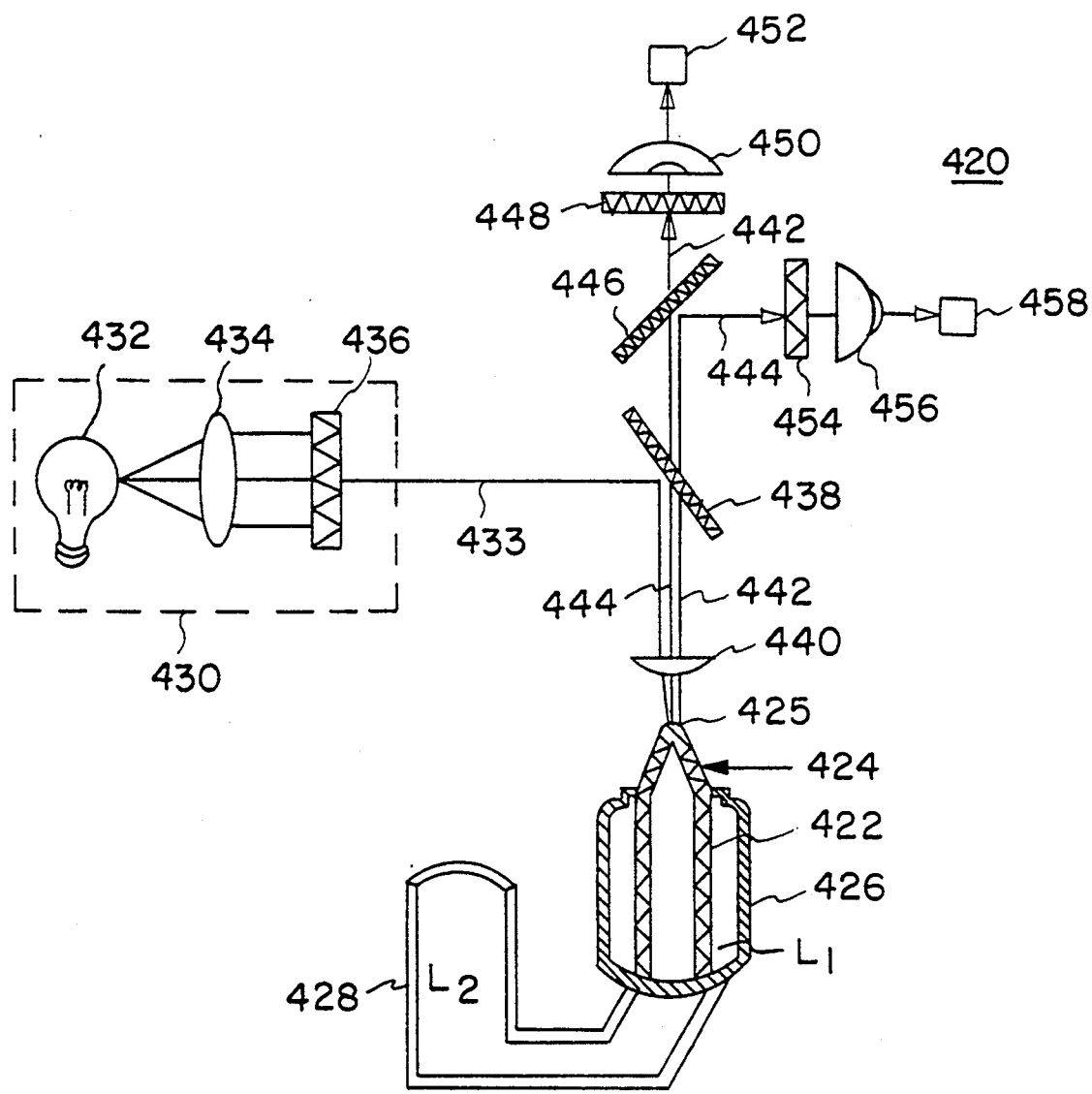
FIG. 13 is a schematic representation of a sensing apparatus according to the invention for detecting two output wavelengths.

An apparatus 420 according to the invention for delivering excitation radiation to a sensor 422 through a launcher 424 is shown in FIG. 13. The sensor 422 is installed in a first reservoir 426 which allows a first liquid $L_1$ to contact the outer surface of the sensor 422. Inside of the sensor 422 is connected to a second reservoir 428 which contains liquid $L_2$ that is drawn by capillary action into the inside of the sensor 422. The construction of the sensor or launcher should incorporate an appropriately placed vent hole for air escape on contact with the medium. Light source 430 produces coherent excitation light 432 at a first wavelength. In this example, the source 430 includes a tungsten lamp which produces noncolummated radiation that is collected by a lens 432 and passed through an interference filter 436 to produce the excitation wavelength 433. The excitation radiation 433 is reflected by first dichroic beam splitter 438 and is passed through launch lens 440 which focuses the radiation upon radiation port 425 of the launcher 424.

The apparatus 420 is constructed to monitor two output wavelengths 442 and 444. The output radiation emerges through radiation port 425 and is directed by the lens 440 through the first beam splitter 438 to a second dichroic beam splitter 446 which passes a first emission wavelength 442 and reflects the second output radiation 444 which is at a different wavelength. The first output wavelength 442 passes through interference filter 448 which blocks wavelengths other than those of interest. The radiation is focused by lens 450 upon first detector 452 which converts the first radiation output signal 442 to an electronic signal. Similarly, the second output radiation 444 passes through an interference filter 454 and focusing lens 456, whereupon it impinges upon second detector 458 which produces a second electronic output signal. The actual excitation and emission wavelengths are selected as described above for FIGS. 3–10C.

Although specific features of the invention are shown in some drawings and not in others, it is for convenience only as each feature may be combined with any or all of the other features in accordance with the invention.

It should be understood, however, that the foregoing description of the invention is intended merely to be illustrative thereof and that other modifications, embodiments, and equivalents may be apparent to those skilled in the art without departing from its spirit.

We claim:

1. An evanescent wave sensor comprising:
   a) a single waveguide having at least a first wave propagating surface and a second wave propagating surface, said waveguide propagating at least one radiation input along said waveguide between said first and second surfaces, and emitting at least one radiation output signal(s);
   b) said first surface being coated with an analyte specific reagent and being capable of receiving a radiation signal to detect a first analyte interacting with the surface; and
   c) said second surface being coated with a second analyte specific reagent and a fluorescent reference material or a fluorescent reference material wherein said second surface is capable of receiving a radiation signal to detect at least one of a second analyte and said fluorescent reference material or just said fluorescent reference material.

2. The sensor of claim 1 in which said waveguide is a hollow core having an inner surface and an outer surface, one of said inner and outer surfaces forming said first wave propagating surface and the other of said inner and outer surfaces forming said second wave propagating surface.

3. The sensor of claim 1 in which said waveguide is a frustoconical shell having a radiation port at a first end and a base at a second end, the base having a dimension greater than that of the radiation port, said shell having inner and outer wall surfaces extending between the radiation port and the base and being formed of a material having a predetermined refractive index greater than that of a test medium, wherein one of said inner and outer surfaces forms said first wave propagating surface and the other of said inner and outer surfaces forms said second wave propagating surface.

4. The sensor of claim 1 in which said waveguide is a planar element having upper and lower surfaces, wherein one of said upper and lower surfaces forms said first wave propagating surface and the other of said upper and lower surfaces forms said second wave propagating surface.

5. An evanescent wave sensor for receiving at least one light input signal and emitting at least one output signal to detect at least one analyte in a medium, comprising:

a) a single waveguide having at least a first wave propagating surface and a second wave propagating surface, said waveguide propagating the input signal along said waveguide between said first and second surfaces;

b) said first surface having a first reactant coating comprising a binding partner to a first analyte;

c) said second surface having a second reactant coating comprising a binding partner to another analyte and a fluorescent reference material or just a fluorescent reference material; and d) said first and second coated surfaces being capable of receiving a light input and generating a light signal output representing one or more analytes and a fluorescent reference signal from said fluorescent reference material.

6. The sensor of claim 5 in which said waveguide is a hollow core having an inner surface and an outer surface, one of said inner and outer surfaces forming said first wave propagating surface and the other of said inner and outer surfaces forming said second wave propagating surface.

7. The sensor of claim 6 further comprising means for delivering the light input signal to said hollow core.

8. The sensor of claim 7 in which said means for delivering comprises a launcher element having a small-diameter radiation port at a first end and a larger outer diameter at a second end which matches the outer diameter of said waveguide.

9. The sensor of claim 8 in which said launcher element is a tapered hollow core waveguide with a light input first end having a smaller diameter than its second end.

10. The sensor of claim 5 in which said waveguide is a frustoconical shell having a radiation port at a first end and a base at a second end, the base having a dimension greater than that of the radiation port, said shell having inner and outer wall surfaces extending between the radiation port and the base and being formed of a material having a predetermined refractive index greater than that of a test medium, wherein one of said inner and outer surfaces forms said first wave propagating surface and the other of said inner and outer surfaces forms said second wave propagating surface.

11. The sensor of claim 5 in which said first and second wave propagating surfaces propagate radiation between them by total internal reflection along and axis of propagating, and said surfaces are substantially parallel to each other along the axis of propagation.

12. The sensor of claim 5 wherein said first reactant coating and said second reactant coating is an immobilized antibody.

13. The sensor of claim 5 wherein said first reactant coating and said second reactant coating is an immobilized antigen.

14. The sensor of claim 5 wherein said first reactant coating is an enzyme.

15. The sensor of claim 5 wherein said first reactant coating and said second reactant coating is a nucleic acid.

16. The sensor of claim 5 wherein said first reactant coating said second reactant coating is a receptor.

17. The sensor of claim 5 in which said waveguide is transmissive to light which can excite fluorescence of a fluorescent tag and is transmissive to fluorescent radiation from a fluorescent tag bound to an analyte after said analyte is bound to one of said wave propagating surfaces.

18. The sensor of claim 5 further comprising means for isolating said second surface from the medium to which said first surface is exposed.

19. The sensor of claim 18 in which said means for isolating includes a gel containing a reference fluorophore.

20. The sensor of claim 18 in which said means for isolating includes a solid polymeric material containing a reference fluorophore.

21. The sensor of claim 20 in which said means for isolating includes polytetrafluoroethylene-co-hexafluoropropylene.

22. The sensor of claim 5 in which said light signal representing at least one of a second analyte and/or a reference has a magnitude depending on the magnitude of radiation reentering said first surface.

23. An apparatus for analyzing at least on e medium, comprising:

a) a single waveguide having at least a first wave propagating surface and a second wave propagating surface;

b) means for guiding a light input signal into said waveguide from a radiation source such that the input signal is propagated between the first and second surfaces;

c) said first surface being coated with an analyte specific reagent and being capable of receiving a light input and giving a light output signal representing binding of a first analyte to said first surface;

d) said second surface being coated with a second analyte specific reagent and a reference fluorophore material or just a fluorescent reference material and being capable of receiving a light input and giving a light output signal representing binding of at least one of a second analyte to said second surface and the presence of said reference fluorophore material or just the presence of said reference fluorophore material; and e) means for guiding at least one output signal from said waveguide to means for detecting the output signal.

24. A method of spectrophotometrically assaying one or more analytes in at least one medium, comprising:

a) providing a single waveguide having at least a first wave propagating surface and a second wave propagating surface, and having a analyte specific reagent disposed on at least one of the first and second surfaces for reaction with one or more analyte(s) and a fluorescent reference material coated on the second surface;

b) contacting the waveguide with said medium and allowing said one or more analytes to bind to their corresponding analyte specific reagents on said first and second surfaces;

c) contacting the waveguide with a fluroescently labeled analyte specific reagent;

d) propagating radiation along the waveguide to generate evanescent wave electromagnetic fields at both the first and second surfaces to irradiate bound fluorescently labeled analyte specific reagent and said fluorescent reference material; and e) detecting radiation resulting from the irradiation of the bound fluorescently labeled analyte specific reagent and the fluorescent reference material by monitoring radiation emitted from the waveguide.

25. The method of claim 24 in which said waveguide is frustoconical shell.

26. The method of claim 24 in which detecting includes monitoring at least two output signals, wherein a first output signal is generated at said first surface and a second output signal is generated at said second surface.

* * * * *